US012765818B2

(12) United States Patent
Cafferty

(10) Patent No.: US 12,765,818 B2
(45) Date of Patent: Oct. 20, 2026

(54) SYSTEM AND METHOD FOR MEASURING THE PERCENT FILL OF BLOOD SAMPLING CAPILLARY

(71) Applicant: Nova Biomedical Corporation, Waltham, MA (US)

(72) Inventor: Michael Cafferty, Medford, MA (US)

(73) Assignee: NOVA BIOMEDICAL CORPORATION, Waltham, MA (US)

( * ) Notice: Subject to any disclaimer, the term of this patent is extended or adjusted under 35 U.S.C. 154(b) by 1209 days.

(21) Appl. No.: 17/558,912

(22) Filed: Dec. 22, 2021

(65) Prior Publication Data

US 2023/0200693 A1 Jun. 29, 2023

(51) Int. Cl.
*A61B 5/15* (2006.01)

(52) U.S. Cl.
CPC .. *A61B 5/150274* (2013.01); *A61B 5/150022* (2013.01); *A61B 5/150946* (2013.01); *A61B 5/150801* (2013.01); *A61B 2560/0223* (2013.01)

(58) Field of Classification Search
CPC ........ A61B 5/150274; A61B 5/150022; A61B 5/150946; A61B 5/150801; A61B 2560/0223; A61B 5/150961; A61B 5/208; G01F 23/00; G01F 23/292; G06T 7/0012; G06T 7/90; G06V 10/05; G01N 15/1433; G01N 21/25
See application file for complete search history.

(56) References Cited

U.S. PATENT DOCUMENTS

| | | | |
|---|---|---|---|
| 6,960,287 | B2 | 11/2005 | Charlton |
| 7,267,799 | B1 | 9/2007 | Borich et al. |
| 8,012,327 | B2 | 9/2011 | Yamazaki et al. |
| 8,936,713 | B2 | 1/2015 | Rodgers et al. |
| 9,377,475 | B2 | 6/2016 | Emeric et al. |
| 9,670,775 | B2 | 6/2017 | Tjhang et al. |

(Continued)

FOREIGN PATENT DOCUMENTS

| | | |
|---|---|---|
| CN | 106525664 A | 3/2017 |
| CN | 213516762 U | 6/2021 |

(Continued)

OTHER PUBLICATIONS

Kanda, JPH01313759A (translation), 1988 (Year: 1988).*

(Continued)

*Primary Examiner* — Adam J Eiseman
*Assistant Examiner* — Lucy Eppert
(74) *Attorney, Agent, or Firm* — Hayes Soloway PC

(57) ABSTRACT

A system and method for measuring the percent fill of a blood sampling capillary includes a chamber for receiving a sample capillary containing a blood sample, an illuminator arranged to illuminate the sample capillary, an imaging lens aligned with the chamber and the sample capillary, an image sensor aligned with the imaging lens wherein the image sensor receives an image of the blood in the sample capillary from the imaging lens and converts the image to image data, a micro-controller circuit electrically coupled to the image sensor, and at least one of a host computer or a user interface electrically coupled to the micro-controller unit where the micro-controller circuit processes the image data into a percent fill result where the percent fill result is passed to the at least one of the host computer or the user interface.

18 Claims, 5 Drawing Sheets

(56) References Cited

U.S. PATENT DOCUMENTS

| | | | | |
|---|---|---|---|---|
| 10,254,233 | B2 | 4/2019 | Markovsky et al. | |
| 10,722,887 | B2 | 7/2020 | Azpiroz et al. | |
| 10,768,105 | B1 * | 9/2020 | Mohan | G02B 21/084 |
| 10,972,641 | B2 | 4/2021 | Chou et al. | |
| 2004/0142463 | A1 | 7/2004 | Walker et al. | |
| 2005/0177315 | A1 * | 8/2005 | Ghosh | G16B 25/00 702/20 |
| 2009/0263013 | A1 * | 10/2009 | Xiong | G06V 10/56 382/164 |
| 2012/0309636 | A1 | 12/2012 | Gibbons et al. | |
| 2014/0080149 | A1 | 3/2014 | Goehde | |
| 2014/0105446 | A1 | 4/2014 | Maxey et al. | |
| 2015/0260713 | A1 * | 9/2015 | Ghaffari | B01L 3/5055 435/5 |
| 2019/0056384 | A1 | 2/2019 | Gershtein et al. | |
| 2019/0247851 | A1 | 8/2019 | Virey | |
| 2020/0082540 | A1 * | 3/2020 | Roy Chowdhury | G05D 1/0246 |

FOREIGN PATENT DOCUMENTS

| | | | | | |
|---|---|---|---|---|---|
| JP | H01313759 | A * | 6/1988 | | |
| JP | H06221895 | A | 8/1994 | | |
| JP | 2001165752 | A | 6/2001 | | |
| JP | 2005502877 | A | 1/2005 | | |
| JP | 2013088114 | A | 5/2013 | | |
| JP | 2015532428 | A | 11/2015 | | |
| JP | 2018096740 | A | 6/2018 | | |
| KR | 101465933 | B1 * | 3/2014 | G06T 7/90 | |
| WO | 2020141463 | A2 | 7/2020 | | |
| WO | WO-2021002105 | A1 * | 1/2021 | G01N 21/00 | |

OTHER PUBLICATIONS

Saravan, Non-Contact, Opaque Type Liquid Level Indicator, Apr. 2013, Certified Journal, vol. 3, Issue 4, 639-640 (Year: 2013).*
Hong, KR101465933B1 (translation), 2014 (Year: 2014).*
Nakayama, WO-2021002105-A1 (translation), (Year: 2021).*
Lapierre et al., “Principles around Accurate Blood Volume Collection Using Capillary Action”, Langmuir, ACS Publications, American Chemical Society, vol. 33, 2017, pp. 14220-14225, 6 pages.

* cited by examiner

SYSTEM AND METHOD FOR MEASURING THE PERCENT FILL OF BLOOD SAMPLING CAPILLARY

BACKGROUND OF THE INVENTION

1. Field of the Invention

The present invention relates generally to a capillary fill imaging system. Particularly, the present invention relates to a capillary fill imaging system and method for measuring percent fill of blood sampling capillaries.

2. Description of the Prior Art

A multitude of laboratory tests for analytes of interest are performed on biological samples for diagnosis, screening, disease staging, drug testing, pregnancy testing, forensic analysis, and other reasons. Notwithstanding that a few qualitative tests have been reduced to simple kits for the patient's use, the majority of quantitative tests still require the expertise of trained technicians in a laboratory setting using sophisticated instruments.

Recently, there has been developed instruments and systems called point-of-care instruments that are capable of being operated by nurses and/or caregivers in hospitals, urgent care centers, doctor offices, and the like, where reliable results are obtained with minimal instrument training of the nurses and/or caregivers.

In these point-of-care settings, whole blood samples are usually drawn by lancing the skin of the patient and obtaining a blood sample collected by a capillary tube. When using capillary tubes for blood collection, it is imperative that a sufficient amount of blood is collected to perform the desired test, yet, it is desirable to only obtain the required amount of blood. One problem associated with some lancing and/or testing devices is that the requisite amount of blood for accurate test results is not always obtained. Proper blood sample acquisition requires the user to hold the capillary tube to the blood sample until the tube is filled to the appropriate level. If the improper amount is obtained, the test results may be erroneous and a test sample is wasted. More serious an issue, however, is that the user may be relying on inaccurate and erroneous test results when an insufficient sample volume is harvested. Obviously, because of the potentially serious nature of the medical issues involved, erroneous results are to be avoided.

Several prior art devices have attempted to determine fill levels in liquid systems.

U.S. Patent Application Publication US 2014/0105446-A1 (2014, Maxey et al.) discloses a computer-implemented methods, software, and systems for determining a property of a wellbore fluid. A computing system receives an image of a first sample of the wellbore fluid filling a conduit to a threshold volume of the conduit. The computing system determines a first time duration of the first sample of the wellbore fluid filling the conduit to the threshold volume of the conduit based on the image of the first sample. The computing system receives an image of a second sample of the wellbore fluid filling the conduit to the threshold volume of the conduit. The computing system determines a second time duration of the second sample of the wellbore fluid filling the conduit to the threshold volume of the conduit based on the image of the second sample. A property of the wellbore fluid is determined based on a difference between the first and second time durations. This patent publication also mentions using capillary action to fill the conduit tube and to correlate a pixel count of an image based on the fluid level in the tube.

U.S. Pat. No. 6,960,287 (2005, Steven C. Charlton) discloses an underfill detection system for a test sensor. The test sensor includes a capillary channel for collecting the liquid sample and a conductor disposed outside the capillary channel. The conductor is in fluid communication with the capillary channel. As the liquid test sample is collected and moved through the capillary channel, the sample contacts the conductor to signal a full condition.

U.S. Pat. No. 8,936,713 B2 (Rodgers et al., 2015) discloses a fill sufficiency method and system. The system discloses a test strip having a first working electrode, a reference electrode and a second working electrode. In the method, acceptable fill data from known first current and known second current are used to predict an estimated second current at proximate the second time for a given batch of test strips during the test sequence. The estimated second current at proximate the second time interval is then compared with a measured actual second current at proximate the second time interval during an actual test to determine if the measured actual second current is substantially equal to or within an acceptable percent deviation from the estimated second current so as to determine sufficient volume of physiological fluid sample in the test strip.

SUMMARY OF THE INVENTION

Since it is possible for blood testing instruments to run an analysis with less than the required volume of blood, an error can result in the reported values of the analysis. A system for measuring the percent amount of blood filling a capillary is desirable to provide the instrument/analyzer either with a number to use to correct the reported value, or signal to the user that the blood sample was insufficient, and a value cannot be reported, thereby preventing incorrect results from being reported to the user.

As mentioned in the prior art section, certain references describe a capillary under-fill detection system that uses two electrodes to detect the fill level. This requires the addition of electrodes to the capillary, increasing the capillary cost. In another prior art reference, the reference describes the use of an imager to check the flow of a sample in a capillary but does not mention a method to use the imager to measure the sample volume.

It is an object of the present invention to provide a system and method to capture an image of a sample capillary, then analyze the image to determine the percent fill of the capillary.

The present invention achieves these and other objectives by providing a system for measuring the percent fill of a sample capillary. In one embodiment of the present invention, the system includes a chamber for receiving a sample capillary containing a blood sample, an illuminator arranged to illuminate the sample capillary, an imaging lens aligned with the chamber and the sample capillary, an image sensor aligned with the imaging lens wherein the image sensor receives an image of the blood in the sample capillary from the imaging lens and converts the image to image data, a micro-controller circuit electrically coupled to the image sensor, and at least one of a host computer or a user interface electrically coupled to the micro-controller unit where the micro-controller circuit processes the image data into a percent fill result wherein the percent fill result is passed to the at least one of the host computer or the user interface.

In one embodiment of the present invention, the system includes an illuminator that is a white light LED.

In another embodiment of the present invention, the system further includes an aperture structure aligned with the imaging lens and the imaging sensor where the aperture structure is disposed between the imaging lens and the image sensor. The aperture structure restricts a ray cone of the image of the blood in the sample capillary to decrease image distortion and aberrations caused by the imaging lens.

In still another embodiment, the microcontroller circuit controls the illuminator.

In yet another embodiment, the micro-controller circuit includes software that selects out the pixels of the image of the blood-filled capillary whose values lie in a particular range of hue.

In a further embodiment, the software converts the image data into a first type of hue space and a second type of hue space.

In another embodiment, the first type of hue space is a YCbCr format color space.

In one embodiment, the second type of hue space is a HSV format color space.

In one embodiment, the software is an interpreted high-level general-purpose programming language containing a first algorithm to convert the image to a YCbCr format color space and a second algorithm to convert the image to a HSV format color space.

In one embodiment, the image data of the first type of hue space and the image data of the second type of hue space are run through mask-generating functions to create two masks, a mask of the YCbCr color space and a mask of the HSV color space based on a selected hue range, wherein pixels lying within the selected hue range are set to 1 in the mask and pixels outside the selected hue range are set to 0.

In one embodiment, a 1-dimensional array is created from the combination of the two masks.

In one embodiment, the system further includes a reference capillary known to be one hundred percent filled with blood or a reference capillary known to be one hundred percent filled with a blood substitute having a required red hue where image data of the reference capillary establishes a calibration value for determining the percent fill of the sample capillary.

In another embodiment, there is disclosed a method for measuring a percent fill of a sample capillary containing a blood sample. The method includes a) disposing the sample capillary into the system for imaging analysis, b) capturing an image of the of the sample capillary and converting the image to image data, c) submitting the image data from the captured image to a micro-controller circuit containing software that processes the image data into the first type of hue space data and a second type of hue space data, d) submitting the first type of hue space data and the second type of hue space data to corresponding mask-generating functions creating two masks based on a selected hue range, e) creating a 1-dimensional array by combining the two masks, and f) determining a percent fill result of the sample capillary by comparing a value generated by analysis of the 1-dimensional array to a calibration value.

In one embodiment, the determining step includes calculating a difference from a blood sample start location of the blood in the image of the sample capillary and an end location of the blood in the image of the sample capillary, and multiplying the difference by the calibration value.

In one embodiment, a method of creating a calibration value used in the system of claim 1 is disclosed. The method includes creating a calibration value using a reference capillary known to be one hundred percent (100%) filled with blood or a reference capillary known to be one hundred percent (100%) filled with a substitute substance having a required red hue, submitting the reference capillary known to be one hundred percent (100%) filled to steps a), b), c), d), e) previously disclosed, and calculating the calibration value.

DETAILED DESCRIPTION OF THE INVENTION

Figure 1:
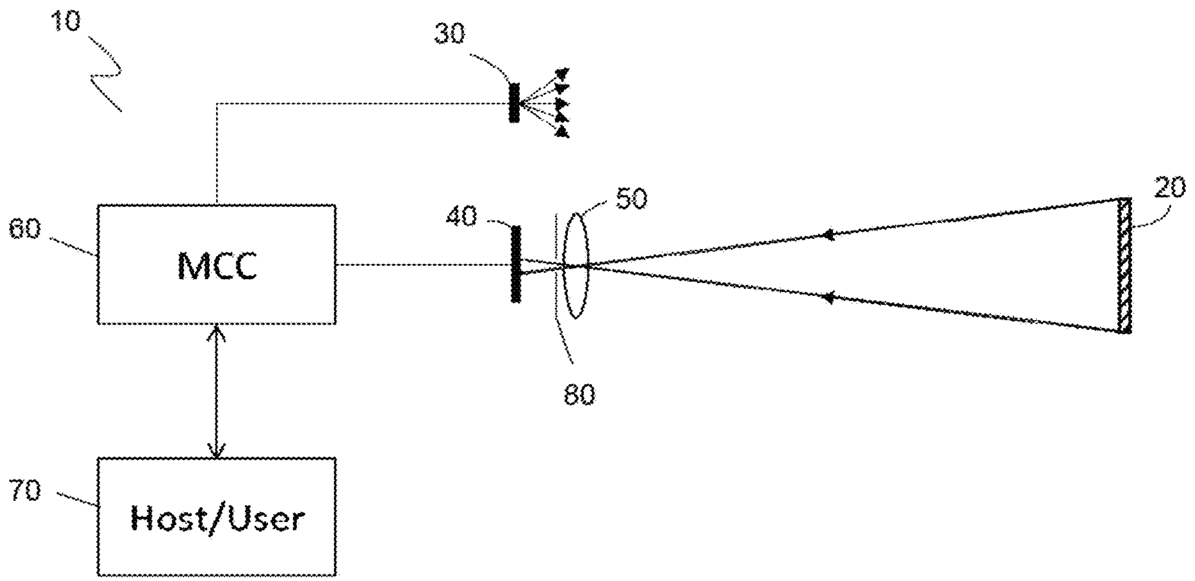
FIG. 1 is a schematic view showing a diagram of the capillary imager of the present invention showing a capillary filled with blood, an illumination source, an image sensor, an imaging lens, an optional aperture structure, a micro-controller circuit, and a host computer or analyzer and/or a user interface.

The embodiments of the present invention are illustrated in FIGS. 1-6. FIG. 1 shows one embodiment of a diagram of the capillary imager system of the present invention. The capillary imager system 10 includes a capillary 20 containing a blood sample to be imaged and a percent fill to be determined, an illumination source 30, an image sensor 40, an imaging lens 50, an optional aperture structure 80, a micro-controller circuit 60, and a host computer or analyzer and/or a user interface 70. The illuminator is a light source such as, for example, a white LED. An image of the capillary 20 is projected onto the image sensor 40 by the imaging lens 50. The image sensor 40 communicates with the micro-controller circuit 60, where the micro-controller circuit 60 also controls the illumination source 30. Image data from the image sensor 40 is processed by the micro-controller circuit, and the results are passed to the host computer or analyzer and/or the user interface 70. The percent fill results may be presented to a user of the system, or for further processing performed by the host computer or analyzer. For example, the host computer may control an entire analyzer with other subsystems, and use the percent fill results from the micro-controller circuit 60 for further calculations and/or corrections of measured analyte values.

Figure 2:
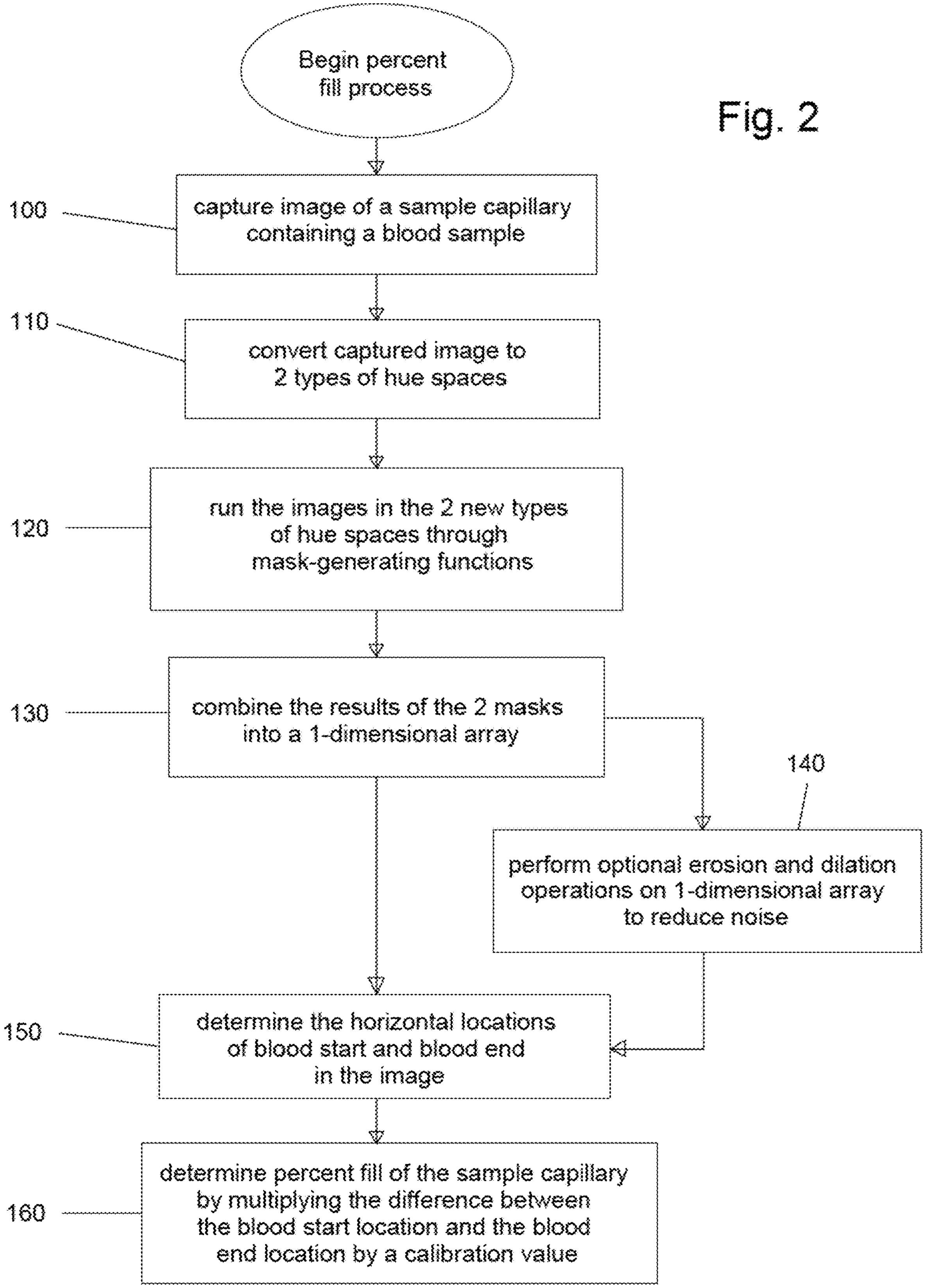
FIG. 2 is a flow chart showing the general steps in the process for determining the percent fill of sample capillary containing a blood sample.

FIG. 2 is an illustration of the process of determining the percent fill of a sample capillary containing a blood sample using the above-described system. A general description of the process is as follows. In step 1 (100), an image of a sample capillary is captured. In Step 2 (110), the captured image is converted to two types of hue space. In Step 3 (120), the images in the two new types of hue spaces are run through mask generating functions, one mask-generating function for each of the two types of hue space. Step 4 (130) then combines the results of the two masks generated into a 1-dimensional array by summing/combining the mask of the first hue space and the mask of the second hue space pixel-by-pixel. In Step 5 (140), the 1-dimensional array is optionally run through erosion and dilation operations to reduce noise. In Step 6 (150), the blood start location 80 and blood end location 82 in the image of the sample capillary 20 is determined. In Step 7 (160), the percent fill of the sample capillary 20 is determined by multiplying the difference between the blood start location 80 and the blood end location 82 by a calibration value.

Process of Calculating the Percent Fill from a Capillary Image

Figure 3:
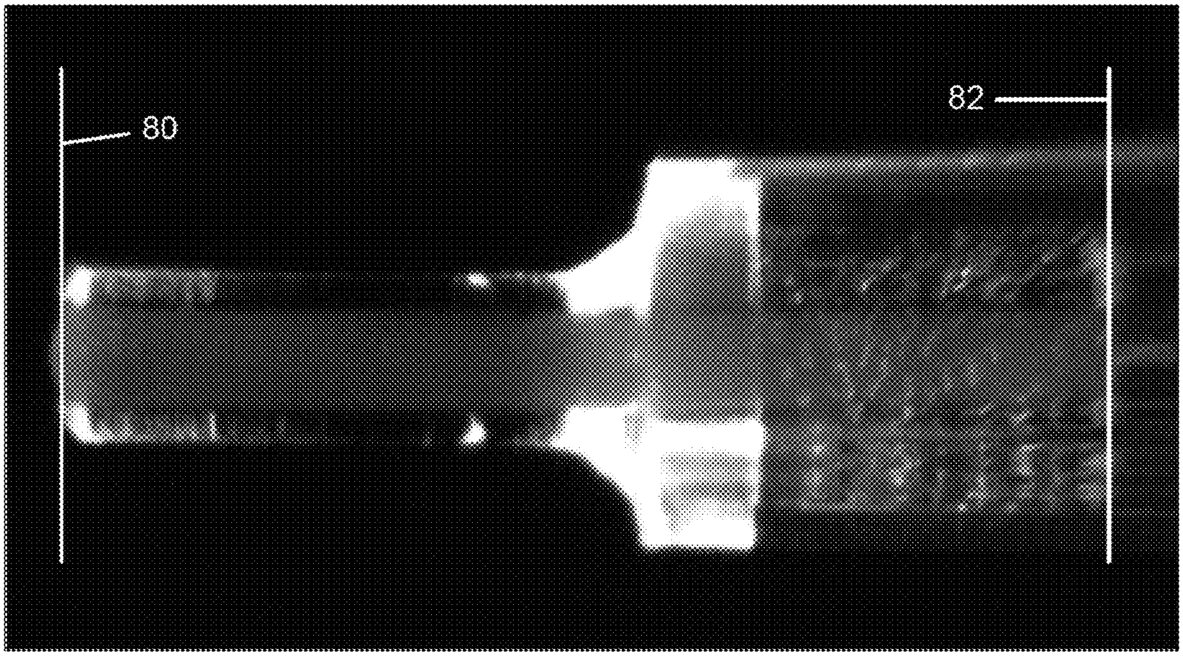
FIG. 3 is a color image of a capillary containing a blood sample showing a one hundred percent filled capillary with blood start and blood end lines.

Turning now to FIG. 3, there is shown a typical image of a capillary containing a blood sample gathered from a system as shown in FIG. 1. For illustrative purposes only, the capillary in the image is filled completely to the one hundred percent (100%) level. The software or code used to calculate the percent fill from a capillary image is written in the Python programming language. Python is an interpreted high-level general-purpose programming language. Its design philosophy emphasizes code readability with its use of significant indentation. Its language constructs as well as its object-oriented approach aim to help programmers write clear, logical code for small and large-scale projects.

Many of the most widely used programming languages (such as C++, Java, Python, etc.) are multi-paradigm and they support object-oriented programming to a greater or lesser degree, typically in combination with imperative, procedural programming. Significant object-oriented languages include: Java, C++, C#, Python, R, PHP, Visual Basic.NET, JavaScript, Ruby, Perl, SIMSCRIPT, Object Pascal, Objective-C, Dart, Swift, Scala, Kotlin, Common Lisp, MATLAB, and Smalltalk. Although the Python language was used, persons skilled in the art are capable of transcribing the method in Python code into any of the object-oriented languages including those listed above.

The next step in the process is to select a region of the capillary containing the blood sample. One way of doing this is to select out the pixels whose values lie in a particular range of hue. In the present invention, the image is converted to two types of hue space: YCbCr and HSV. YCbCr is typically used for digital encoding of color information suited for video, still-image compression and transmission such as MPEG and JPEG. HSV (hue, saturation, value), also known as HSB (hue, saturation, brightness), is often used by artists because it is perceived to be more natural to think about a color in terms of hue and saturation than in terms of additive or subtractive color components. HSV is a transformation of an RGB color space, and its components and colorimetry are relative to the RGB color space from which it was derived. Once converted, the images in the new color spaces are then run through mask generating functions.

The function calls to perform this are:

```
1) Yimg=MT9M114_rgb_to_ycbcr (img)
2) Himg=rgb_to_hsv(img)
3) BWY=createMask(Yimg, 0, 255, 0, 255, 143, 255)
4) BWH=createMaskHSV(Himg, 240, 20, 51, 255, 0, 255)
```

The inputs to the mask-generating calls show the hue range to be selected. Pixels that are in between those values are set to 1 in the mask, pixels outside the ranges are set to 0. The results of the two masks are combined pixel-by-pixel with the following logical AND statement:

```
5) import numpy as np
6) BWYH=np.logical_and(BWY,BWH)
```

The resulting array of 1's and 0's is summed column-wise into a 1-dimensional array:

```
7) sBWYH=np.sum (BWYH,0)
```

Algorithm to Convert Image to YCbCr Format (Python Language)

The following algorithm is used to convert the captured image to YCbCr format using the Python language.

```
import numpy as np
def MT9M114_rgb_to_ycbcr (img):
    img_ycbcr=np.zeros (img.shape)
    Rp=img[ . . . , 0]
    Gp=img[ . . . , 1]
    Bp=img[ . . . , 2]
    img_ycbcr[ . . . , 0]=(0.2126*Rp+0.7152*Gp+
        0.0722*Bp)*(219/256)+16
    img_ycbcr[ . . . , 1]=0.5389*(Bp−img_ycbcr[ . . . ,
        0])*(224/256)+128
    img_ycbcr[ . . . , 2]=0.6350*(Rp−img_ycbor [ . . . ,
        0])*(224/256)+128
    img_ycbcr[img_ycbcr<16]=16
    idx=img_ycbcr[ . . . , 2]>240
    img_ycbcr[idx, 2]=240
    idx=img_ycbcr[ . . . , 1]>240
    img_ycbcr[idx, 1]=240
    idx=img_ycbcr[ . . . , 0]>235
    img_ycbcr[idx, 0]=235
    return img_ycbcr.astype(np.uint8)
```

Algorithm to Convert Image to HSV Format (Python Language)

The following algorithm is used to convert the captured image to HSV format using the Python language.

```
import numpy as np
def rgb_to_hsv (img):
    out=np.zeros (img.shape)
    #Calculate V
    V=img.max(−1)
    out[ . . . , 2]=V
    #Calculate S
    delta=img.ptp(−1)
    #Ignore warning for zero divided by zero
    old_settings=np.seterr(invalid='ignore')
    out[ . . . , 1]=255.*delta/V
    out[delta==0., 1]=0.
    #Calculate H
    X=img.min(−1)
    #If R is max and G is min
    idx=np.logical_and((img[ . . . , 0]==V),(img[ . . . ,
        1]==X))
    out[idx, 0]=5.+(V[idx]−img[idx, 2])/delta[idx]
    #If R is max and G is not min
    idx=np.logical_and((img[ . . . , 0]==V),np.logical_not
        ((img[ . . . , 1]==X)))
    out[idx, 0]=1.−(V[idx]−img[idx, 1])/delta[idx]
    #If G is max and B is min
    idx=np.logical_and((img[ . . . , 1]==V), (img[ . . . ,
        2]==X))
    out[idx, 0]=1.+(V[idx]−img[idx, 0])/delta[idx]
    #If G is max and B is not min
    idx=np.logical_and((img[ . . . , 1]==V),np.logical_not
        ((img[ . . . , 2]==X)))
    out[idx, 0]=3.−(V[idx]−img[idx, 2])/delta[idx]
    #If B is max and R is min
    idx=np.logical_and((img[ . . . , 2]==V), (img[ . . . ,
        0]==X))
    out[idx, 0]=3.+(V[idx]−img[idx, 1])/delta[idx]
    #If B is max and R is not min
    idx=np.logical_and((img[ . . . , 2]==V),np.logical_not
        ((img[ . . . , 0]==X)))
    out[idx, 0]=5.−(V[idx]−img[idx, 0])/delta[idx]
```

out[ . . . , 0]=(255./6.)*out[ . . . , 0]

out[delta==0.]=0.

np.seterr(**old_settings)

Remove NaNs out[np.isnan(out)]=0.

return out.astype(np.uint8)

Algorithm to Create Hue Masks (Python Language)

The following algorithm is used to create the hue masks using the Python language.

import numpy as np def createMask(img, min0, max0, min1, max1, min2, max2):

mask0=np.logical_and(img[:,:,0]>=min0, img[:,:,0]<=max0)

mask1=np.logical_and(img[:,:,1]>=min1, img[:,:,1]<=max1)

mask2=np.logical_and(img[:,:,2]>=min2, img[:,:,2]<=max2)

return np.logical_and(mask0,np.logical_and(mask1, mask2)

import numpy as np def createMaskHSV (img, min0, max0, min1, max1, min2, max2):

mask0=np.logical_or(img[:,:,0]>=min0, img[:,:, 0]<=max0)

mask1=np.logical_and(img[:,:,1]>=min1, img[:,:, 1]<=max1)

mask2=np.logical_and(img[:: 2]>=min2, img[:,: 2]<=max2)

return np.logical_and(mask0,np.logical_and(mask1, mask2))

Algorithm to Find Threshold Transitions (Python Language)

The following algorithm is used to find the threshold transitions from the column-wise 1-dimensional array calculated in Step 7 (placed into variable "f," which is a vector list of numbers where the term "f[n]" below refers to the nth number of "f").

```
def findThreshold(T,f):
  loc = [ ]
  upSlope = True
  for n in range (f.shape [0]):
    if f[n] > T and upSlope:
      loc.append (n)
      upSlope = False
    elif f[n] < T and not upSlope:
      loc.append (n)
      upSlope = True
  return loc
```

Figure 4:
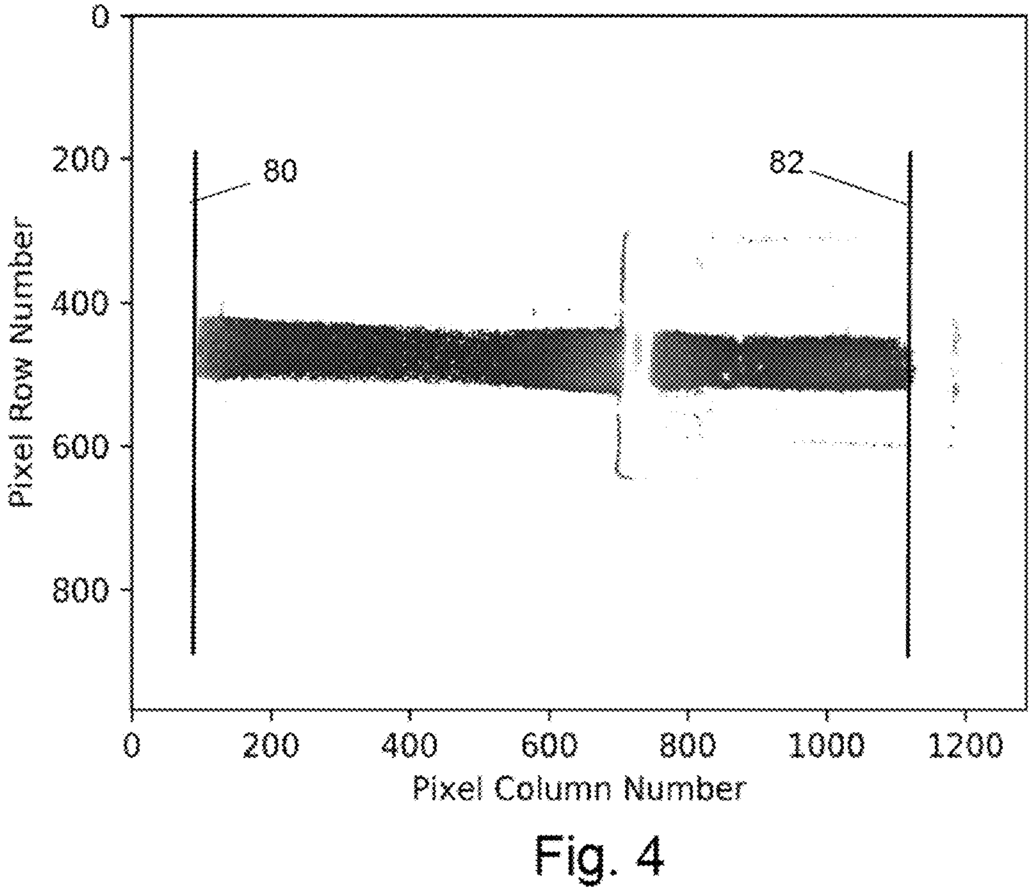
FIG. 4 is a color image mask of a partially filled capillary separated by hue.

Turning now to FIG. 4, FIG. 4 shows the region of the image of a partially-filled capillary that has been masked by the logical AND of the two generated masks, showing the selection of the regions with the reddish color.

Figure 5:
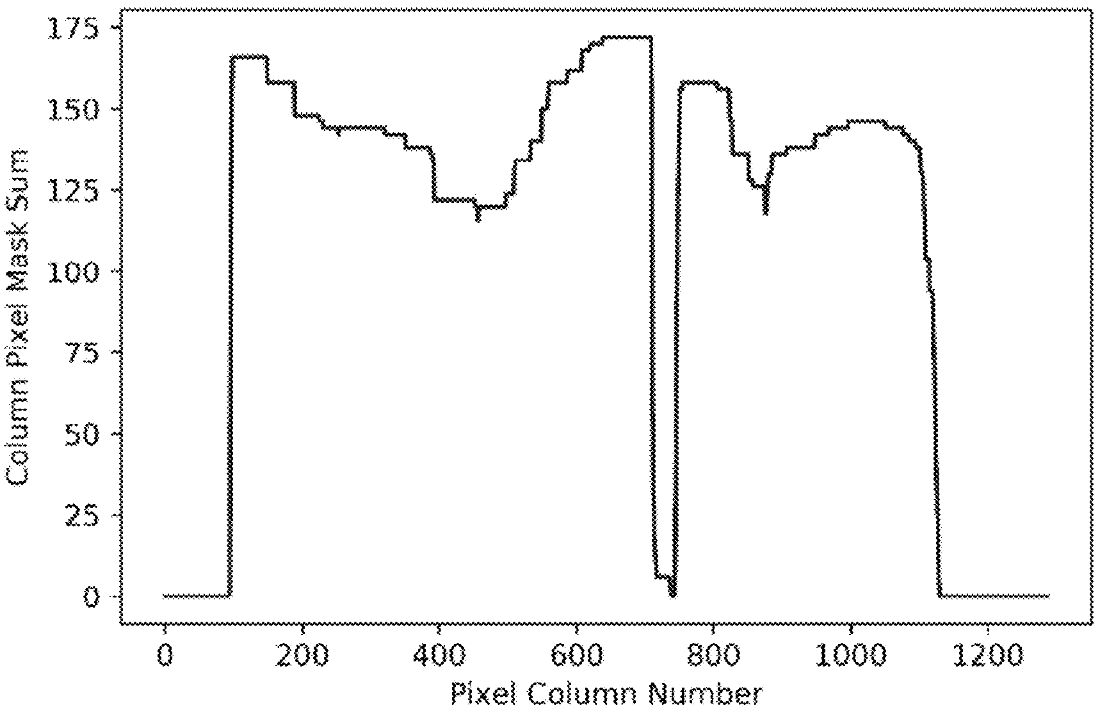
FIG. 5 is a graphical representation of the pixel column sum of the mask.

FIG. 5 is an illustration/graph of the column-wise 1-dimensional array calculated in Step 6, the summing of the values in the columns of the logical AND of the two generated masks. This plot is a function of the horizontal direction and shows how many pixels with the selected hue are in each vertical column. The array sBWYH is then optionally run through erosion and dilation operations to reduce noise:

8) sBWYH=ndimage.grey_erosion(sBWYH, structure=np.ones((50,)))

9) sBWYH=2*ndimage.grey_dilation(sBWYH, structure=np.ones((50,)))

The array sBWYH is then put through the function findThreshold, which finds the horizontal locations of transitions greater than the specified threshold of 40:

10) locs=findThreshold(40, sBWYH)

The start of the blood in the capillary is a blood start location 80, the end of the blood in the capillary is a blood end location 82:

11) bloodStart=min(locs)

12) bloodEnd=max(locs)

The percent fill value is the difference between the blood start location 80 and the blood end location 82, multiplied by a calibration value (calVal).

13) pontFill=(bloodEnd−bloodStart)×calVal

Determination of Calibration Value (calVal)

The calibration value is previously determined, using a reference capillary known to be 100% filled with blood or a substitute such as red dye or red epoxy. The image from this calibration/reference capillary is run through the same processing steps, with the exception that step 13 is skipped and the step 14 below is used to calculate the calibration value:

14) calVal=100.0/(bloodEnd−bloodStart)

The calibration/reference capillary can be filled with any substance of the required red hue. One formulation used that works consists of a mixture of 0.30 grams of UV cure clear epoxy NOA 81 and 0.06 grams of Congo Red dye powder Sigma C6277-25G (lot MKCF4499 with a dye content of 95%). The mixture is forced into the capillary with a syringe and needle until it is 100% full, then cured with a UV cure lamp.

Figure 6:
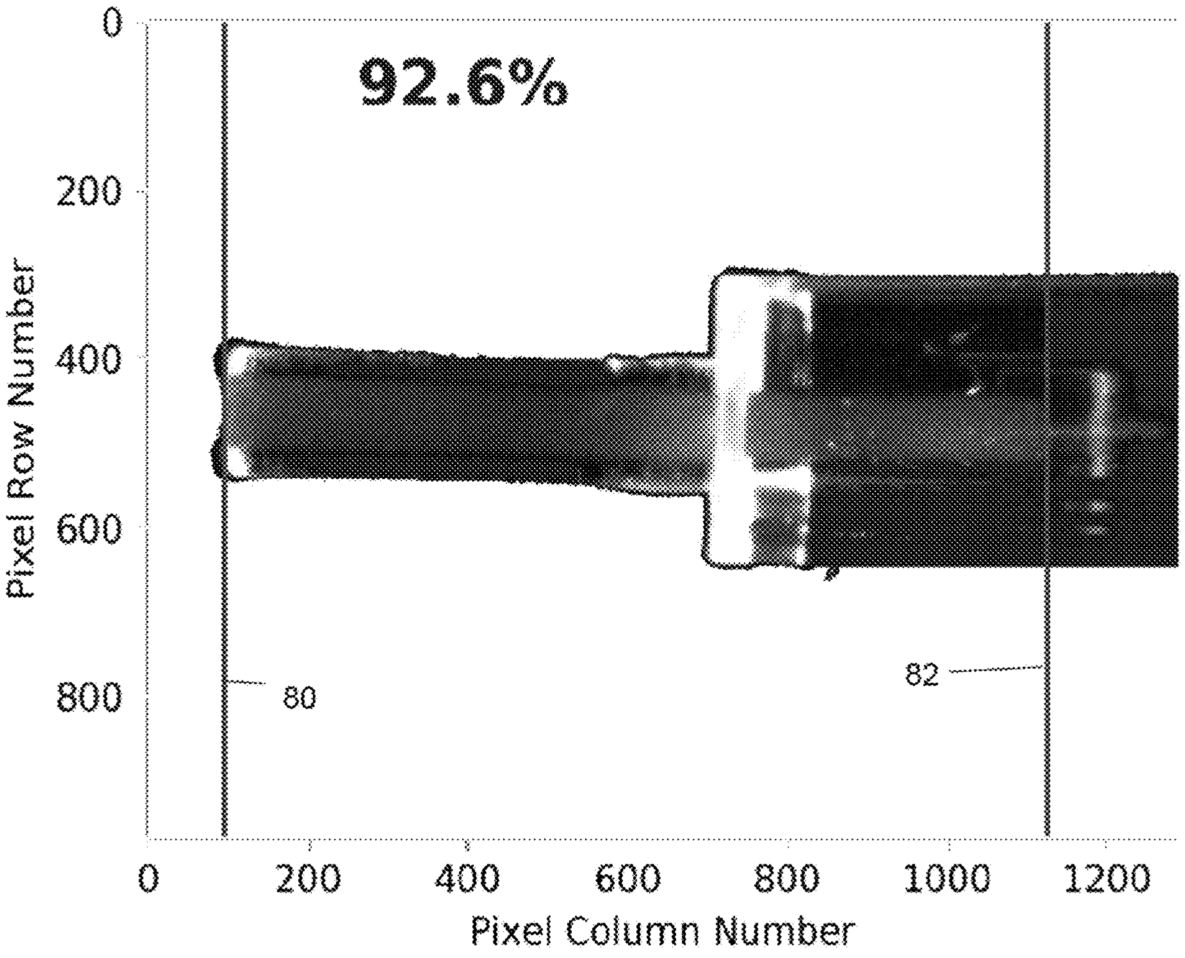
FIG. 6 is a calculated result of the capillary fill overlayed on the capillary image for a partially-filled capillary showing vertical lines where the algorithm determined the beginning and end of the blood in the capillary.

FIG. 6 shows the resulting percent fill calculation for the partially filled capillary. The vertical lines in the figure are blood start 80 and blood end 82 locations.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A system configured for measuring a percent fill of a blood sampling capillary containing a blood sample, the system comprising:

a chamber configured for receiving the blood sampling capillary containing the blood sample;

an illuminator configured to illuminate the blood sampling capillary;

an imaging lens aligned with the chamber and the blood sampling capillary;

an image sensor aligned with the imaging lens, wherein the image sensor is configured to:

receive an image of the blood sample contained in the blood sampling capillary from the imaging lens; and convert the image of the blood sample contained in the blood sampling capillary to image data;

an aperture structure aligned with the imaging lens and the image sensor, wherein the aperture structure is configured to reduce image distortion and aberrations caused by the imaging lens by restricting the image of the blood sample contained in the blood sampling capillary to a ray cone which is received by the image sensor; and a micro-controller circuit electrically coupled to the image sensor and configured to:

generate first image data from the image data and convert the first image data to a first image in a first type of hue space;

generate second image data from the image data and convert the second image data to a second image in a second type of hue space which differs from the first type of hue space;

combine, into a one-dimensional array, (a) a first mask generated based on the first image in the first type of hue space and (b) a second mask generated based on the second image in the second type of hue space; and determine the percent fill of the blood sampling capillary containing the blood sample utilizing a predetermined calibration value obtained from analyzing image data of a reference capillary having a known percentage fill of blood or a blood substitute having a red hue;

wherein in being configured to determine the percent fill of the blood sampling capillary containing the blood sample utilizing the predetermined calibration value, the micro-controller circuit is configured to multiply (a) a difference between (i) a blood start location determined from the image of the blood sample contained in the blood sampling capillary and (ii) a blood end location determined from the image of the blood sample contained in the blood sampling capillary by (b) the predetermined calibration value;

wherein the system is configured to transmit the percent fill of the blood sampling capillary containing the blood sample to at least one of a computer and a user interface.

2. The system of claim 1, wherein the illuminator comprises a light-emitting diode (LED) configured to emit white light.

3. The system of claim 1, wherein the micro-controller circuit is further configured to control the illuminator.

4. The system of claim 1, wherein the micro-controller circuit is further configured to select out pixels of the image of the blood sample contained in the blood sampling capillary whose values lie in a particular range of hue.

5. The system of claim 1, wherein at least one of:

the first type of hue space is a YCbCr format color space; and the second type of hue space is a HSV format color space.

6. The system of claim 1, wherein:

the first type of hue space is a YCbCr format color space; and the second type of hue space is a HSV format color space.

7. The system of claim 1, wherein the known percentage fill is one hundred percent (100%).

8. The system of claim 1, further comprising the reference capillary.

9. The system of claim 1, wherein the micro-controller circuit is further configured to determine the blood start location and the blood end location by finding one or more horizontal locations of transitions greater than a specified threshold value which identify the blood start location or the blood end location.

10. The system of claim 1, wherein the micro-controller circuit is further configured to at least one of:

perform an erosion operation on the one-dimensional array to reduce noise; and perform a dilation operation on the one-dimensional array to reduce noise.

11. The system of claim 1, wherein the micro-controller circuit is further configured to both:

perform an erosion operation on the one-dimensional array to reduce noise; and perform a dilation operation on the one-dimensional array to reduce noise.

12. The system of claim 1, wherein in being configured to combine the first mask and the second mask into the one-dimensional array, the micro-controller circuit is configured to sum the first mask and the second mask pixel by pixel.

13. The system of claim 12, wherein in being configured to sum the first mask and the second mask pixel by pixel, the micro-controller circuit is configured to sum the first mask and the second mask column-wise into the one-dimensional array.

14. The system of claim 1, wherein the micro-controller circuit is further configured to generate the first mask and the second mask based on a selected hue range, wherein:

pixels lying within the selected hue range are set to 1 in the first mask and the second mask; and pixels outside the selected hue range are set to 0 in the first mask and the second mask.

15. The system of claim 1, wherein the blood substitute comprises at least one of a red dye or a red epoxy.

16. The system of claim 1, wherein the blood substitute comprises an ultraviolet-curable epoxy and a red dye powder.

17. The system of claim 1, further comprising at least one of the computer and the user interface.

18. A system configured for measuring a percent fill of a blood sampling capillary containing a blood sample, the system comprising:

a chamber configured for receiving the blood sampling capillary containing the blood sample;

an illuminator configured to illuminate the blood sampling capillary;

an imaging lens aligned with the chamber and the blood sampling capillary;

an image sensor aligned with the imaging lens, wherein the image sensor is configured to:

receive an image of the blood sample contained in the blood sampling capillary from the imaging lens; and convert the image of the blood sample contained in the blood sampling capillary to image data;

an aperture structure aligned with the imaging lens and the image sensor, wherein the aperture structure is configured to reduce image distortion and aberrations caused by the imaging lens by restricting the image of the blood sample contained in the blood sampling capillary to a ray cone which is received by the image sensor; and a micro-controller circuit electrically coupled to the image sensor and configured to:

generate first image data from the image data and convert the first image data to a first image in a first type of hue space;

generate second image data from the image data and convert the second image data to a second image in a second type of hue space which differs from the first type of hue space;

combine, into a one-dimensional array, (a) a first mask generated based on the first image in the first type of hue space and (b) a second mask generated based on the second image in the second type of hue space; and determine the percent fill of the blood sampling capillary containing the blood sample utilizing a predetermined calibration value obtained from analyzing image data of a reference capillary having a known percentage fill of blood or a blood substitute having a red hue;

wherein:

the micro-controller circuit is further configured to generate the first mask and the second mask based on a selected hue range, wherein:

pixels lying within the selected hue range are set to 1 in the first mask and the second mask; and pixels outside the selected hue range are set to 0 in the first mask and the second mask;

in being configured to combine the first mask and the second mask into the one-dimensional array, the micro-controller circuit is configured to sum the first mask and the second mask pixel by pixel column-wise into the one-dimensional array;

in being configured to determine the percent fill of the blood sampling capillary containing the blood sample utilizing the predetermined calibration value, the micro-controller circuit is configured to multiply (a) a difference between (i) a blood start location determined from the image of the blood sample contained in the blood sampling capillary and (ii) a blood end location determined from the image of the blood sample contained in the blood sampling capillary by (b) the predetermined calibration value;

the micro-controller circuit is further configured to determine the blood start location and the blood end location by finding one or more horizontal locations of transitions greater than a specified threshold value which identify the blood start location or the blood end location; and the system is configured to transmit the percent fill of the blood sampling capillary containing the blood sample to at least one of a computer and a user interface.

* * * * *